(12) United States Patent
Chen et al.

US011091457B2

(10) Patent No.: US 11,091,457 B2
(45) Date of Patent: Aug. 17, 2021

(54) SYNTHETIC NICOTINE COMPOSITION

(71) Applicant: Yunnan Xike Science & Technology Co., Ltd., Yunnan (CN)

(72) Inventors: Zheng Chen, Fujian (CN); Yinghui Cao, Yunnan (CN); Ningning Yan, Yunnan (CN); Songfeng Wang, He'nan (CN); Yong Zhang, Yunnan (CN); Yuefeng Chen, Anhui (CN); Zhennan Huang, Jiangxi (CN); Shenghong Yuan, Yunnan (CN)

(73) Assignee: YUNNAN XIKE SCIENCE & TECHNOLOGY CO., LTD., Kunming (CN)

( * ) Notice: Subject to any disclaimer, the term of this patent is extended or adjusted under 35 U.S.C. 154(b) by 0 days.

(21) Appl. No.: 16/734,413

(22) Filed: Jan. 6, 2020

(65) Prior Publication Data
US 2021/0061783 A1    Mar. 4, 2021

(30) Foreign Application Priority Data

Sep. 3, 2019   (CN) .......................... 201910826162.3

(51) Int. Cl.
| | | |
|---|---|---|
| *C07D 401/04* | (2006.01) | |
| *C07C 233/07* | (2006.01) | |
| *C07C 237/22* | (2006.01) | |
| *C07C 25/08* | (2006.01) | |
| *C07C 53/02* | (2006.01) | |
| *C07C 53/08* | (2006.01) | |
| *C07C 53/126* | (2006.01) | |
| *C07C 57/10* | (2006.01) | |
| *C07C 57/12* | (2006.01) | |
| *C07C 59/08* | (2006.01) | |
| *C07C 59/185* | (2006.01) | |
| *C07C 59/265* | (2006.01) | |
| *C07C 63/06* | (2006.01) | |
| *C07D 207/04* | (2006.01) | |
| *C07D 233/58* | (2006.01) | |
| *C07D 235/06* | (2006.01) | |
| *C07D 241/04* | (2006.01) | |

(52) U.S. Cl.
CPC ............ *C07D 401/04* (2013.01); *C07C 25/08* (2013.01); *C07C 53/02* (2013.01); *C07C 53/08* (2013.01); *C07C 53/126* (2013.01); *C07C 57/10* (2013.01); *C07C 57/12* (2013.01); *C07C 59/08* (2013.01); *C07C 59/185* (2013.01); *C07C 59/265* (2013.01); *C07C 63/06* (2013.01); *C07C 233/07* (2013.01); *C07C 237/22* (2013.01); *C07D 207/04* (2013.01); *C07D 233/58* (2013.01); *C07D 235/06* (2013.01); *C07D 241/04* (2013.01)

(58) Field of Classification Search
CPC .. C07D 401/04; C07D 207/04; C07D 233/58; C07D 235/06; C07D 241/04; C07C 25/08; C07C 53/02; C07C 53/08; C07C 53/126; C07C 57/10; C07C 57/12; C07C 59/08; C07C 59/185; C07C 59/265; C07C 63/06; C07C 233/07; C07C 237/22
See application file for complete search history.

(56) References Cited

U.S. PATENT DOCUMENTS

| | | | | |
|---|---|---|---|---|
| 2008/0286340 | A1* | 11/2008 | Andersson | ............... A61P 25/28 424/440 |
| 2010/0298345 | A1* | 11/2010 | Cashman | ................. A61P 35/00 514/256 |
| 2017/0112182 | A1* | 4/2017 | Arnold | ................... A24F 47/008 |

FOREIGN PATENT DOCUMENTS

| | | |
|---|---|---|
| CN | 107011321 A | 8/2017 |
| CN | 107536099 A | 1/2018 |
| CN | 108323791 A | 7/2018 |
| CN | 109171010 A | 1/2019 |
| CN | 109619655 A | 4/2019 |

\* cited by examiner

*Primary Examiner* — Doan T Phan

(57) ABSTRACT

A synthetic nicotine composition comprising synthetic nicotine, a synthetic nicotine salt and a synthetic nicotine derivative, wherein the synthetic nicotine, the synthetic nicotine salt, and the synthetic nicotine derivative are in mass percentage; the synthetic nicotine accounts for 1-20%, the synthetic nicotine salt accounts for 30-70%, and the synthetic nicotine derivative accounts for 20-50%; and the synthetic nicotine is one or more of S-nicotine and a mixture of R-nicotine containing a racemate and S-nicotine. The synthetic nicotine, synthetic nicotine salt and synthetic nicotine derivative according to the present invention are proportionally mixed to prepare an existing synthetic nicotine product, which relieves the problem of the impact of impurities in natural extracted nicotine products causing an unpleasant smell, a bitter taste and a strong volatility, and can be used in the fields of low temperature heat-not-burn products, snuff, electronic cigarettes, nicotine release patches, insecticides, herbicides, microbicides, drug synthesis, etc.

5 Claims, 5 Drawing Sheets

SYNTHETIC NICOTINE COMPOSITION

CROSS-REFERENCE TO PRIOR APPLICATION

This application claims the benefit of Chinese Patent Application No. 201910826162.3 filed on Sep. 3, 2019, the contents of which are incorporated herein by reference.

TECHNICAL FIELD

The present invention relates to the technical field of synthetic nicotine, and in particular to a synthetic nicotine composition.

BACKGROUND ART

Nicotine, also referred to as nicotinamide, is a viscous, colorless or pale yellow oily liquid found primarily in Solanaceae plants. Nicotine is a physiological excitant that diffuses throughout the body via the lung mucosa and oral mucosa and binds to the nicotinic acetylcholine receptors (nAChRs) on the surface of many neurons after entering the brain, thereby causing the release of neurotransmitters such as dopamine, which causes a sensation of excitement and pleasure and reduces anxiety and stress reaction. Currently, there are studies showing that nicotine has a positive effect, to some extent, on the treatment of Parkinson's disease, Alzheimer's disease, schizophrenia, ulcerative colitis and depression.

Nicotine products currently available on the market are mainly natural nicotine, which is extracted from tobacco raw materials. It contains some impurities, mainly including impurities formed by means of degradation and some trace alkaloid impurities, such as anatabine, muscarine, cotinine, myosmine, β-nicotyrine and nicotinamide-N-oxide. Depending on the place of origin and the quality of the raw materials, the types and contents of impurities in natural nicotine products vary. Since these impurities in natural extracted nicotine products are very similar to nicotine, they are difficult to technically remove. Furthermore, the European Pharmacopoeia, the British Pharmacopoeia and the United States Pharmacopoeia also limit the contents of nicotine impurities to varying degrees. In addition, nicotine extracted from tobacco sources has an unpleasant smell, a bitter taste and a strong volatility, and is easily oxidized into dark red in the air, which all greatly limit the application thereof.

Currently, researches on nicotine are mainly focused on nicotine salts, nicotine complexes, etc. For example, Patent CN 107536099 A discloses a nicotine salt and a preparation method therefor; Patent CN 108323791 A discloses a nicotine-zinc oxide complex, a preparation method therefor and a tobacco product comprising same; Patent CN 109619655 A discloses a complex nicotine salt and a solution thereof, and a preparation method therefor and the use thereof; and Patent CN 109171010 A discloses liquid nicotine and a preparation method therefor. However, all of these patents relate to using nicotine extracted from tobacco sources as a raw material, and have many problems as mentioned above. Patent CN 107011321 A discloses a method for preparing an artificially synthesized racemic nicotine, by means of which high-purity racemic nicotine is successfully synthesized, indicating that nicotine can be synthesized by means of a chemical route. However, there are few reports on the application of synthetic nicotine products.

SUMMARY OF THE INVENTION

In view of the technical problems existing in the background art, the present invention proposes a synthetic nicotine composition.

The present invention proposes a synthetic nicotine composition comprising synthetic nicotine, a synthetic nicotine salt and a synthetic nicotine derivative, wherein the synthetic nicotine, the synthetic nicotine salt, and the synthetic nicotine derivative are in mass percentage; the synthetic nicotine accounts for 1-20%, the synthetic nicotine salt accounts for 30-70%, and the synthetic nicotine derivative accounts for 20-50%; the synthetic nicotine is one or more of S-nicotine and a mixture of R-nicotine containing a racemate and S-nicotine; the synthetic nicotine salt is formed by reacting the synthetic nicotine with an organic acid mixture; and the nicotine derivative comprises one or more of an imidazole derivative of nicotine, an amine derivative of nicotine, and an amino acid derivative of nicotine.

Preferably, the synthesis organic acid mixture for the synthetic nicotine salt is made up of an essential organic acid base compounded with one or more of formic acid, acetic acid, malic acid, citric acid, levulinic acid, lactic acid, aspartic acid, lauric acid, 2-methyl-2-pentenoic acid, linoleic acid and palmitic acid.

Preferably, the essential organic acid base in the synthesis organic acid mixture comprises benzoic acid, sorbic acid and linolenic acid, wherein the benzoic acid, sorbic acid and linolenic acid are in mass percentage, and the benzoic acid accounts for 50-80%, the sorbic acid accounts for 1-20%, and the linolenic acid accounts for 10-30%.

Preferably, the imidazole derivative of nicotine comprises one of or a mixture of some of imidazole, 5-methylimidazole, 2-ethylimidazole, 4,5-dimethylimidazole, benzimidazole, and 3,4-dimethylbenzimidazole.

Preferably, the amine derivative of nicotine comprises one of or a mixture of some of tetrahydropyrrole, 1-methylpiperazine, 3,4-dichlorobenzene, and p-acetylaniline.

Preferably, the amino acid derivative of nicotine comprises one of or a mixture of both of a glycine methyl ester derivative of nicotinamide and a proline methyl ester derivative of nicotinamide.

The beneficial effects of the present invention are as follows: the present synthetic nicotine composition is prepared as an existing synthetic nicotine product by using synthetic nicotine as a basic mixing material, synthesizing a synthetic nicotine salt by using synthetic nicotine, and further proportionally mixing the synthetic nicotine salt and the synthetic nicotine derivative with the basic mixing material, thereby relieving the problem of the impact of impurities in natural extracted nicotine products causing an unpleasant smell, a bitter taste and a strong volatility, and the yield of nicotine is improved by means of synthesis, so that it can be used in the fields of low temperature heat-not-burn products, snuff, electronic cigarettes, nicotine release patches, insecticides, herbicides, microbicides, drug synthesis, etc.

DETAILED DESCRIPTION OF EMBODIMENTS

The technical solution of the embodiments of the present invention will be clearly and completely described below in conjunction with the accompanying drawings for the embodiments of the present invention; and obviously, the embodiments described are merely some, rather than all, of the embodiments of the present invention.

Example 1

Figure 1:
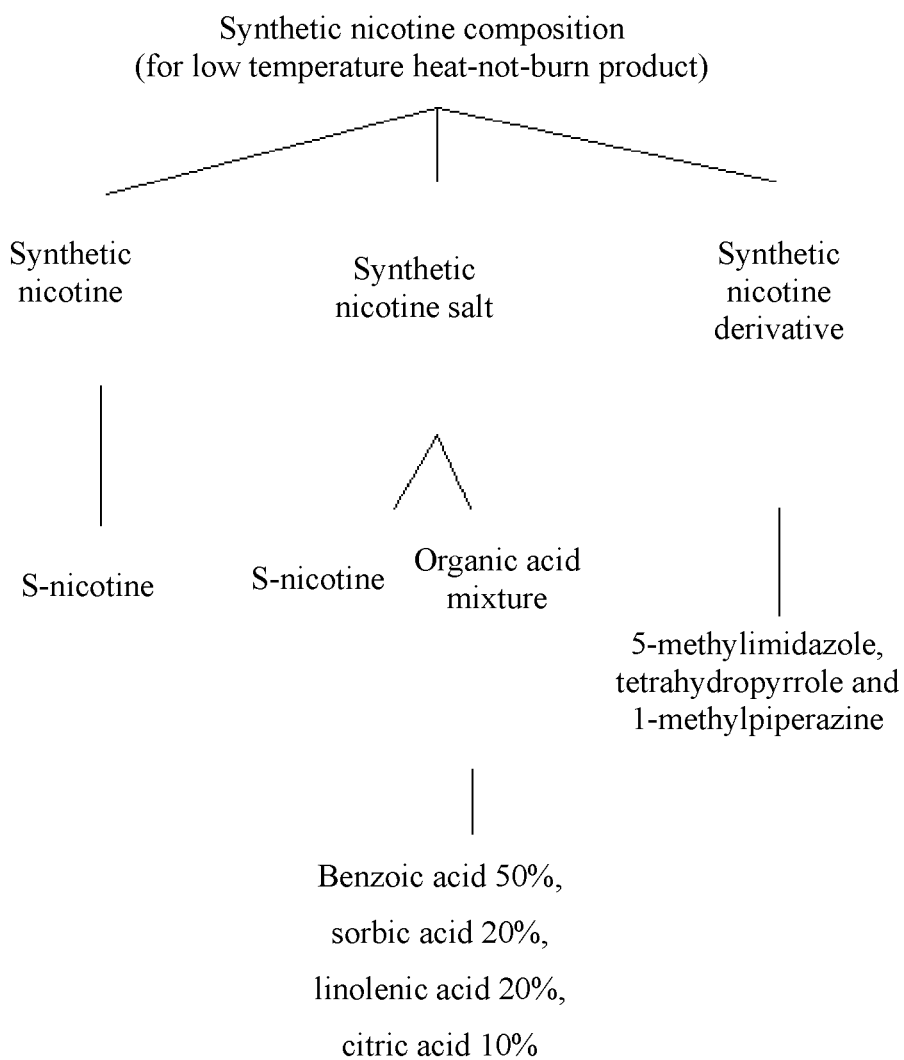
FIG. 1 is a schematic view showing a combination of components in Example 1 of a synthetic nicotine composition proposed by the present invention.

As shown in FIG. 1, a synthetic nicotine composition comprising 1% of pure synthetic S-nicotine, 70% of a synthetic nicotine salt, and 29% of a mixture of nicotine derivatives of 5-methylimidazole derivative, tetrahydropyrrole derivative and 1-methylpiperazine. The synthetic nicotine salt in the composition is formed by reacting pure synthetic S-nicotine with an organic acid mixture. The organic acid mixture contains: 50% of benzoic acid, 20% of sorbic acid, 20% of linolenic acid, and 10% of citric acid. The composition can be used for a low temperature heat-not-burn product.

Example 2

Figure 2:
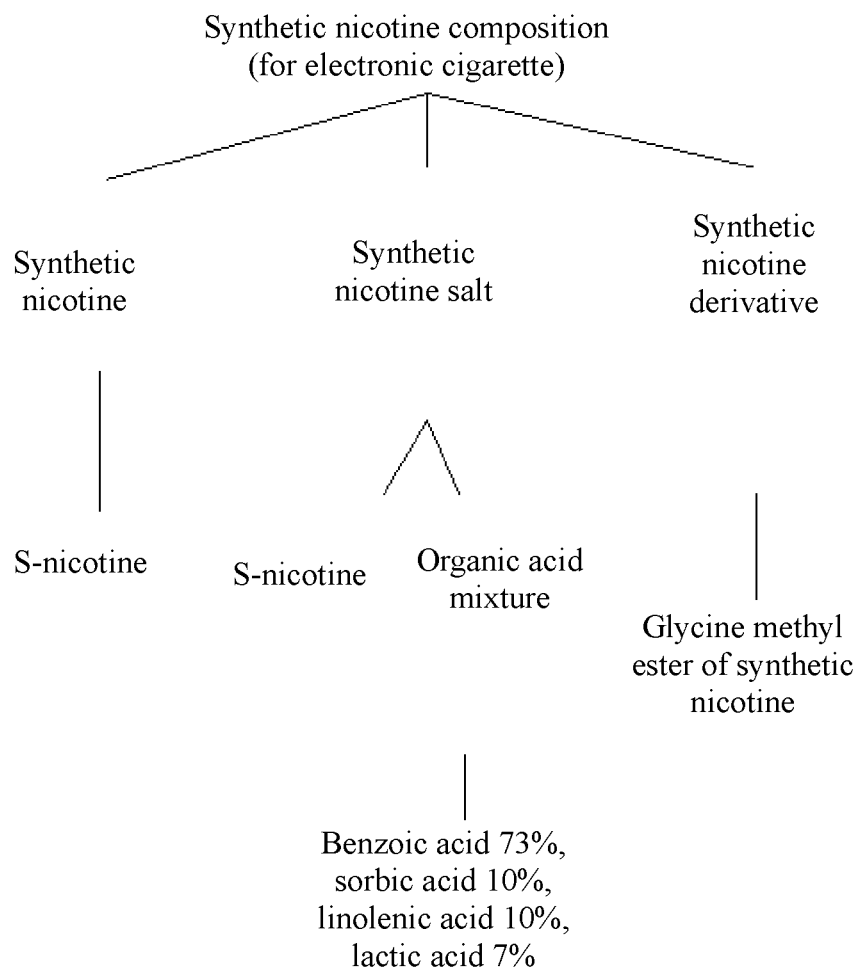
FIG. 2 is a schematic view showing a combination of components in Example 2 of a synthetic nicotine composition proposed by the present invention.

As shown in FIG. 2, a synthetic nicotine composition comprising a mixture of 20% of pure synthetic S-nicotine, 50% of a synthetic nicotine salt, and 30% of a glycine methyl ester of synthetic nicotine. The synthetic nicotine salt in the composition is formed by reacting pure synthetic S-nicotine with an organic acid mixture. The organic acid mixture contains: 73% of benzoic acid, 10% of sorbic acid, 10% of linolenic acid, and 7% of lactic acid. The composition can be used for an electronic cigarette product.

Example 3

Figure 3:
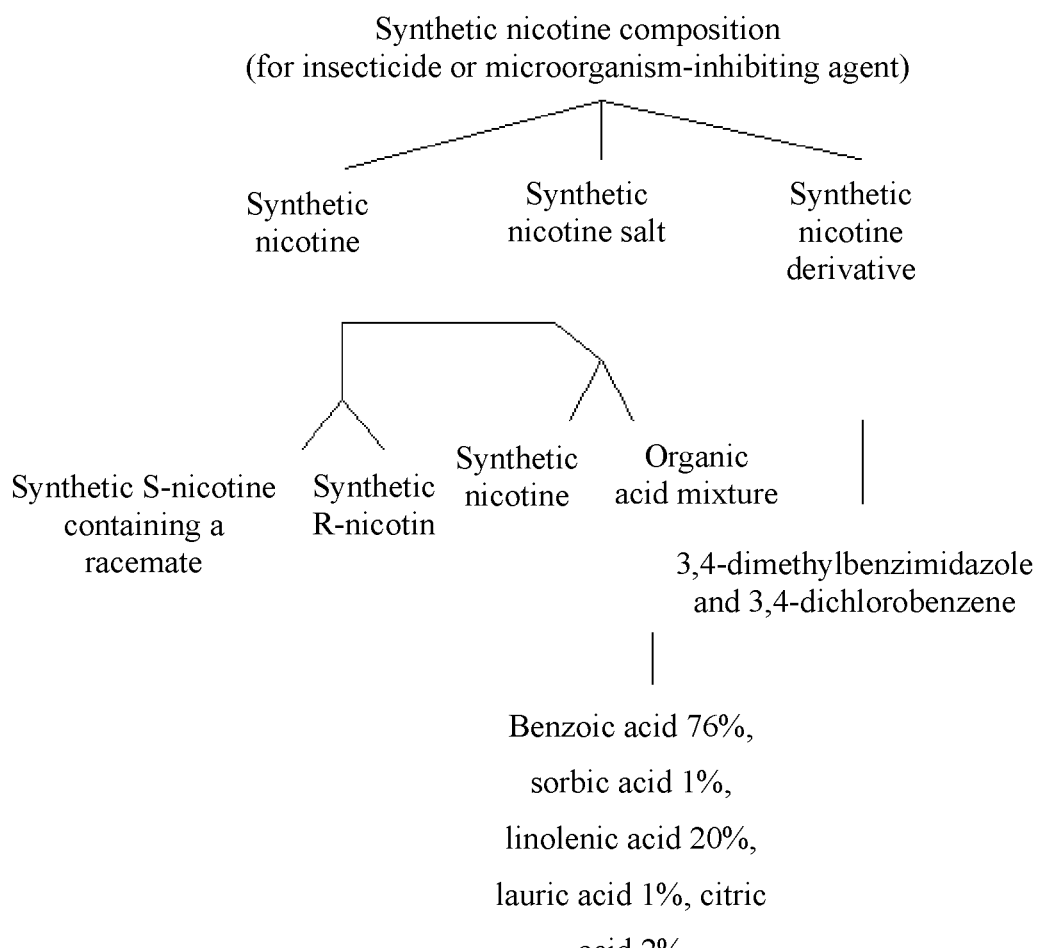
FIG. 3 is a schematic view showing a combination of components in Example 3 of a synthetic nicotine composition proposed by the present invention.

As shown in FIG. 3, a synthetic nicotine composition comprising 20% of a mixture of synthetic S-nicotine containing a racemate and synthetic R-nicotine, 30% of a synthetic nicotine salt, 50% of a mixture of synthetic nicotine derivatives of 3,4-dimethylbenzimidazole and 3,4-dichlorobenzene. The synthetic nicotine salt in the composition is formed by reacting a mixture of synthetic S-nicotine containing a racemate and synthetic R-nicotine with an organic acid mixture. The organic acid mixture contains: 76% of benzoic acid, 1% of sorbic acid, 20% of linolenic acid, 1% of lauric acid, and 2% of citric acid. The composition can be used for an insecticide or a microbicide.

Example 4

Figure 4:
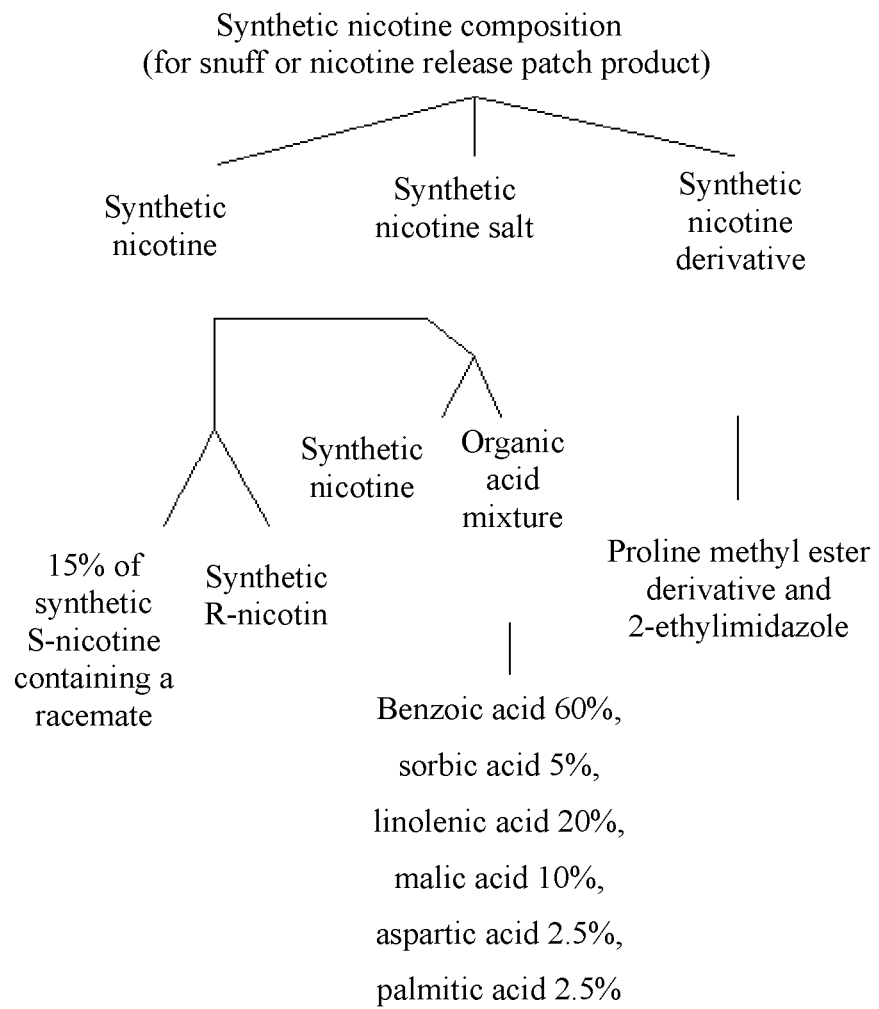
FIG. 4 is a schematic view showing a combination of components in Example 4 of a synthetic nicotine composition proposed by the present invention.

As shown in FIG. 4, a synthetic nicotine composition comprising 15% of a mixture of synthetic S-nicotine containing a racemate and synthetic R-nicotine, 65% of a synthetic nicotine salt, and 20% of a mixture of synthetic nicotine derivatives of proline methyl ester and 2-ethylimidazole. The synthetic nicotine salt in the composition is formed by reacting a mixture of synthetic S-nicotine containing a racemate and synthetic R-nicotine with an organic acid mixture. The organic acid mixture contains: 60% of benzoic acid, 5% of sorbic acid, 20% of linolenic acid, 10% of malic acid, 2.5% of aspartic acid, and 2.5% of palmitic acid. The composition can be used for a snuff or nicotine release patch product.

Example 5

Figure 5:
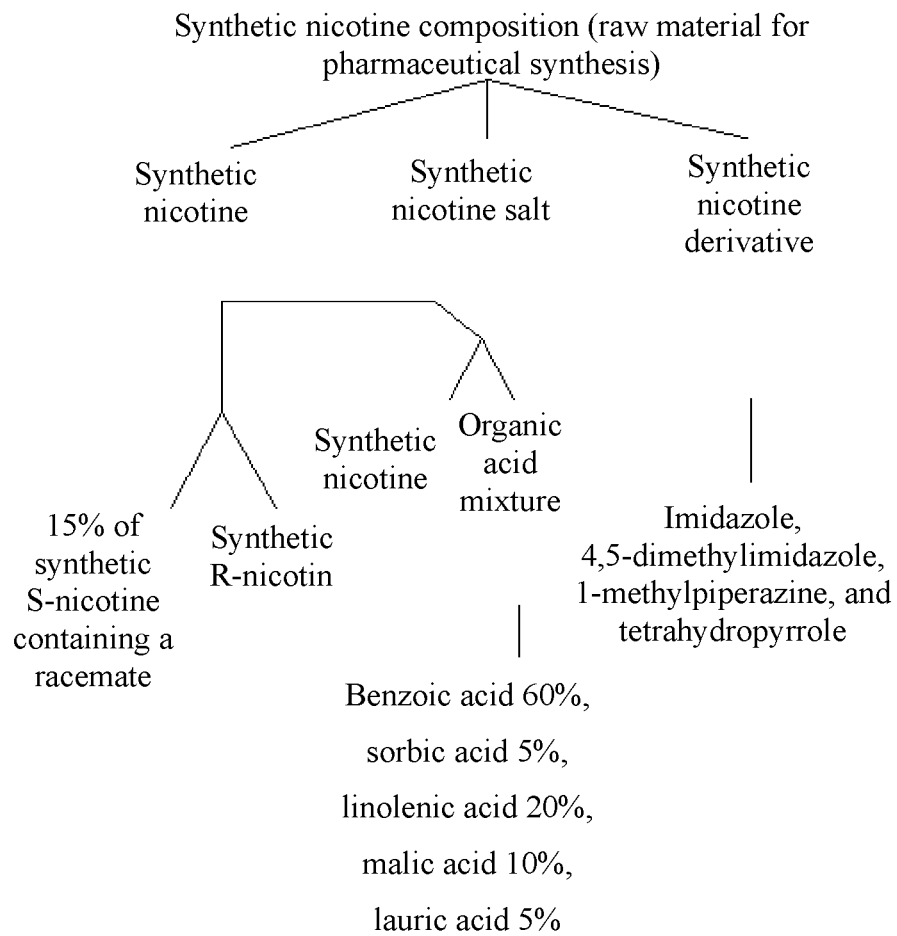
FIG. 5 is a schematic view showing a combination of components in Example 5 of a synthetic nicotine composition proposed by the present invention.

As shown in FIG. 5, a synthetic nicotine composition comprising 15% of a mixture of synthetic S-nicotine containing a racemate and synthetic R-nicotine, 30% of a synthetic nicotine salt, and 55% of a mixture of synthetic nicotine derivatives of imidazole, 4,5-dimethylimidazole, 1-methylpiperazine, and tetrahydropyrrole. The synthetic nicotine salt in the composition is formed by reacting pure synthetic S-nicotine with an organic acid mixture. The organic acid mixture contains: 60% of benzoic acid, 5% of sorbic acid, 20% of linolenic acid, 10% of malic acid, and 5% of lauric acid. The composition can be used as a raw material for pharmaceutical synthesis.

The above description only relates to preferred embodiments of the present invention; however, the protection scope of the present invention is not limited thereto, and any equivalent replacements or modifications made by those skilled in the art according to the technical solution of the present invention and the inventive concept thereof within the technical scope disclosed by the present invention are all intended to be included within the protection scope of the present invention.

The invention claimed is:

1. A synthetic nicotine composition comprising synthetic nicotine, a synthetic nicotine salt and a synthetic nicotine derivative, wherein the synthetic nicotine, the synthetic nicotine salt, and the synthetic nicotine derivative are in mass percentage; the synthetic nicotine accounts for 1-20%, the synthetic nicotine salt accounts for 30-70%, and the synthetic nicotine derivative accounts for 20-50%; the synthetic nicotine is S-nicotine or a racemic mixture of R-nicotine and S-nicotine; the synthetic nicotine salt is formed by reacting the synthetic nicotine with an organic acid mixture; and the nicotine derivative comprises one or more selected from the group consisting of an imidazole derivative of nicotine, an amine derivative of nicotine, and an amino acid derivative of nicotine;

wherein the imidazole derivative of nicotine comprises imidazole, 5-methylimidazole, 2-ethylimidazole, 4,5-dimethylimidazole, benzimidazole, 3,4-dimethylbenzimidazole, or mixtures thereof.

2. The synthetic nicotine composition according to claim 1, wherein the organic acid mixture is made up of an essential organic acid base compounded with one or more selected from the group consisting of formic acid, acetic acid, malic acid, citric acid, levulinic acid, lactic acid, aspartic acid, lauric acid, 2-methyl-2-pentenoic acid, linoleic acid and palmitic acid.

3. The synthetic nicotine composition according to claim 2, wherein the essential organic acid base in the organic acid mixture comprises benzoic acid, sorbic acid and linolenic acid, wherein the benzoic acid, sorbic acid and linolenic acid are in mass percentage, and the benzoic acid accounts for 50-80%, the sorbic acid accounts for 1-20%, and the linolenic acid accounts for 10-30%.

4. The synthetic nicotine composition according to claim 1, wherein the amine derivative of nicotine comprises tetrahydropyrrole, 1-methylpiperazine, 3,4-dichlorobenzene, p acetylaniline, or mixtures thereof.

5. The synthetic nicotine composition according to claim 1, wherein the amino acid derivative of nicotine comprises a glycine methyl ester derivative of nicotinamide, a proline methyl ester derivative of nicotinamide, or a mixture thereof.

\* \* \* \* \*